United States Patent [19]
Barnicki et al.

[11] Patent Number: 5,945,550
[45] Date of Patent: Aug. 31, 1999

[54] GAS PHASE PROCESS FOR THE EPOXIDATION OF NON-ALLYLIC OLEFINS

[75] Inventors: Scott Donald Barnicki; John Robert Monnier, both of Kingsport; Kimberly Thornton Peters, Piney Flats, all of Tenn.

[73] Assignee: Eastman Chemical Company, Kingsport, Tenn.

[21] Appl. No.: 09/122,027

[22] Filed: Jul. 24, 1998

[51] Int. Cl.$^6$ .................................................. C07D 301/10
[52] U.S. Cl. .............................................................. 549/534
[58] Field of Search ............................................. 549/534

[56] References Cited

U.S. PATENT DOCUMENTS

| | | |
|---|---|---|
| 3,119,837 | 1/1964 | Kingsley et al. . |
| 4,897,498 | 1/1990 | Monnier et al. . |
| 4,950,773 | 8/1990 | Monnier et al. . |
| 5,057,481 | 10/1991 | Bhasin . |
| 5,081,096 | 1/1992 | Monnier et al. . |
| 5,117,012 | 5/1992 | Stavinoha, Jr. et al. . |
| 5,138,077 | 8/1992 | Monnier et al. . |
| 5,145,968 | 9/1992 | Monnier et al. . |
| 5,362,890 | 11/1994 | Stavinoha, Jr. et al. . |

FOREIGN PATENT DOCUMENTS

| | | |
|---|---|---|
| 1286687 | 7/1991 | Canada . |
| 2053404 | 12/1992 | Canada . |

OTHER PUBLICATIONS

F. P. Lee, "Loss Prevention in the Process Industries", vol. 1, (1980),485–486.

R. D. Coffee, "Loss Prevention", vol. 13, (1980), 74–80.

*Primary Examiner*—Bernard Dentz
*Attorney, Agent, or Firm*—Matthew W. Smith; Bernard J. Graves, Jr.; Harry J. Gwinnell

[57] ABSTRACT

This invention provides an improved gas phase feed process using heterogeneous catalysis for the selective epoxidation of non-allylic olefins wherein the epoxidation is carried out in the presence of branched-chain alkane or cyclic aliphatic hydrocarbons with high autoignition temperatures and high Research Octane Numbers. The hydrocarbons useful in the present invention possess higher heat capacities as compared to other non-oxidizable materials, e.g., nitrogen, argon, helium, and other straight-chain hydrocarbons, e.g., methane, ethane, and n-butane, as well as smaller flammability (cool flame and explosive) regions than the above-stated hydrocarbons typically used as diluents or ballast gases in olefin epoxidations. The process is particularly useful for the continuous preparation of 3,4-epoxy-1-butene from 1,3-butadiene.

21 Claims, 2 Drawing Sheets

GAS PHASE PROCESS FOR THE EPOXIDATION OF NON-ALLYLIC OLEFINS

FIELD OF THE INVENTION

This invention belongs to the field of synthetic organic chemistry. In particular, it relates to an improved gas phase feed process using heterogeneous catalysis for the selective epoxidation of non-allylic olefins wherein the epoxidation is carried out in the presence of branched-chain alkane or cyclic aliphatic hydrocarbons with high autoignition temperatures and high Research Octane Numbers.

BACKGROUND OF THE INVENTION

Processes for the selective epoxidation of olefins which contain no allylic hydrogen atoms (non-allylic olefins) or olefins which contain hindered allylic hydrogen atoms are described in U.S. Pat. Nos. 4,897,498, 4,950,773, 5,081,096, 5,138,077 and 5,145,968. U.S. Pat. No. 5,117,012 describes the selective epoxidation of 1,3-butadiene to 3,4-epoxy-1-butene (EpB) by contacting a mixture comprising 1,3-butadiene, oxygen and methane with a supported silver catalyst at elevated temperatures. U.S. Pat. No. 5,362,890 describes an improved process for the selective epoxidation of 1,3-butadiene to 3,4-epoxy-1-butene (EpB) wherein the ballast gas for the reaction is n-butane. U.S. Pat. No. 5,618,954 describes a similar process for the epoxidation of 1,3-butadiene to 3,4-epoxy-1-butene with nitrogen or $C_1$–$C_4$ hydrocarbons (especially methane) as the diluent.

The use of diluent or ballast gases in ethylene epoxidation is described in Canadian Patents 1,286,687 and 2,053,404 and U.S. Pat. Nos. 3,119,837 and 5,057,481. According to these patents, the typical molar composition of feed gases used in such ethylene epoxidation processes comprise up to 30 mole percent ethylene, up to 12 mole percent oxygen, up to 7 mole percent carbon dioxide, up to 5 mole percent ethane with the balance being composed of an additional inert diluent such as nitrogen or methane. U.S. Pat. No. 3,119, 837 teaches that selectivity of ethylene conversion to ethylene oxide can be enhanced by the addition of methane as a diluent. Methane serves as a heat sink, moderating temperature differentials within the reactor, and allows for more isothermal reactor operation. This patent further states that the benefits to selectivity and ease of operation do not extend to other paraffins normally encountered in commercially available ethylene, e.g., ethane and propane. Use of methane also allows an increase in the oxygen:ethylene ratio in the reactor feed gas which increases conversion of ethylene to ethylene oxide.

According to Canadian Patent 1,286,687, other diluents that function as heat sinks include nitrogen, helium, argon, carbon dioxide and lower paraffins such as methane and ethane. However, U.S. Pat. No. 5,057,481 teaches that the use of ethane at concentrations greater than about 5 mole percent results in reduced selectivity in the epoxidation of ethylene to ethylene oxide and lower thermal stability because the chloride concentration on the catalyst surface is lowered. Typical silver catalysts employed in the epoxidation of ethylene contain about 1 to 300 parts by million by weight (ppmw) of Cl on the catalyst surface, both to increase selectivity to ethylene oxide by lowering combustion of ethylene and ethylene oxide to carbon dioxide and water as well as to increase the thermal stability of the silver catalyst. If the level of Cl on the surface of the silver catalyst becomes too low, the reaction becomes excessively exothermic with accompanying loss of selectivity. Ethane acts as a chloride stripping agent and at concentrations above 5 mole percent and at temperatures typically employed in the epoxidation of ethylene, e.g., 240 to 280° C., the degree of chloride stripping becomes unacceptably excessive. As is disclosed in the above-cited patents, one of the problems associated with the use of carbon dioxide as a heat transfer agent (heat sink) in ethylene epoxidation processes is that at levels greater than about 7 mole percent, the carbon dioxide becomes a reaction inhibitor for ethylene oxide formation. Thus, the concentration of carbon dioxide in feed gas in ethylene epoxidation processes must be limited to concentrations of less than about 7 mole percent. At such low levels carbon dioxide does not have an appreciable effect on the heat capacity nor the flammability characteristics of the gas mixture.

As explained in Lees, F. P., "Loss Prevention in the Process Industries, Volume 1," 485–86 (1980) and Coffee, R. D., Loss Prevention 13, 74–80, (1980), a flammable gas, e.g., methane, butane, and other alkane hydrocarbons, burns in oxidizing environments only over a limited composition range. The limits of flammability (often called the explosive or hot flame limits) are the concentration extremes at which a mixture of a flammable gas and an oxidant can continue to burn once a flame is ignited by an external energy source such as a spark. These flammability extremes are a function of temperature, pressure, and composition. The explosive limit is usually expressed as volume or mole percent flammable gas in a mixture of oxidant (usually oxygen), inert, and flammable gas. The smaller value is the lower (lean) limit and the larger value is the upper (rich) limit. For example methane-oxygen mixtures will propagate flames for methane concentrations between 5.1 and 61 mole percent methane and methane-air mixtures between 5.3 and 14 mole percent methane, at 25° C. and atmospheric pressure. In general the lower explosive limit (LEL) decreases, and the upper explosive limit (UEL) increases as temperature and pressure increase, and amount of inert decreases.

Autoignition is defined as the spontaneous ignition of a vapor-air mixture as the result of the heat generated from exothermic oxidation reactions and in the absence of an external energy source such as a spark. The autoignition temperature (hereafter AIT) is the lowest temperature at which such an ignition will occur. Under these conditions the combustion of the flammable material generally goes to completion, i.e., carbon dioxide and water products. The combustion reactions can be very rapid and violent, i.e., explosive. The AIT is also a function of the composition, temperature, and pressure. A temperature rise of 800 to 200° C. is expected with generation of a severe, destructive pressure pulse. Thus, if the reaction composition were in the flammable region and above the AIT, the mixture would spontaneously ignite or explode even without an initiating external energy source, with the ensuing destructive consequences to the reactor and potential hazardous vapor release.

At temperatures well below the autoignition temperature, oxidizable materials can also exhibit cool flame behavior, in which a partial oxidation mechanism prevails. Temperature rises of 10 to 200° C. are common, without the severe pressure pulse associated with a hot flame. The transition between a cool and hot flame is ill-defined. In spite of the more mild consequences of the cool flame, this condition represents a potential safety concern, as it may lead to runaway epoxidation reaction and subsequent explosive behavior, as well as a loss of valuable product and diluent gases. Thus, from a safety and operational standpoint it is desirable to maintain the reactor composition, temperature, and pressure outside of both the cool and hot flame regions.

The use of diluent gases in non-allylic olefin epoxidation, specifically the epoxidation of 1,3-butadiene to 3,4-epoxy-1-butene, is described in U.S. Pat. Nos. 5,362,890, and 5,618,954. U.S. Pat. No. 5,618,954 teaches that nitrogen and $C_1$–$C_4$ paraffinic hydrocarbons, especially methane, or mixtures therein are the preferred diluents for the epoxidation of 1,3-butadiene to 3,4-epoxy-1-butene The oxygen:butadiene ratio in the reactor feed gas can be increased by using methane as the diluent over that with nitrogen as the diluent without the methane:oxygen:butadiene mixture becoming flammable.

U.S. Pat. No. 5,362,890 discloses the use of $C_2$–$C_6$ paraffin hydrocarbons as diluents for non-allylic olefin epoxidation. The data disclosed in this patent clearly teaches the advantages of using higher alkane hydrocarbons over methane, nitrogen and other common diluents. Advantages cited include higher safe oxygen levels, higher epoxide production levels for the same reactor temperatures, and more stable operation due to better heat removal. This patent specifically states that the use of branched-chain alkanes is not preferred over straight-chain paraffins due to the reactivity of tertiary hydrogen atoms of such branched-chain hydrocarbons with the surface chloride atoms of the silver catalyst. As with ethylene epoxidation, excessive stripping of chlorine from the surface of the silver catalyst tends to lower the selectivity of the epoxidation of non-allylic olefins.

U.S. Pat. No. 5,362,890 also teaches that straight-chain alkanes, e.g., normal butane, normal pentane, normal hexane, are preferred diluents, and that normal butane is the most preferred diluent for the epoxidation of 1,3-butadiene to 3,4-epoxy-1-butene. Although the use of n- butane increases the overall heat capacity of the reactor feed gas markedly over the heat capacity with methane or nitrogen as the diluent, at high oxygen concentrations, i.e., greater than about 20 mole percent, which are favorable for increased epoxide production, and with highly active catalysts, temperature gradients in a fixed bed reactor can be excessive, thereby resulting in unstable and unsafe operation. Branched-chain diluents are not preferred.

However, for straight-chain alkanes, as the number of carbon atoms in the diluent is increased from $C_4$ Up to $C_5$ and $C_6$, e.g., n-pentane and n-hexane, the autoignition temperature of the diluent and the size of the cool flame region increases. The AIT drops in the series n-butane, n- pentane, n-hexane as 372° C., 258° C., 227° C. respectively. In fact, at high concentrations of oxygen and at the higher end of the preferred range of reactor temperatures, the reactor composition can easily be in the cool flame or explosive flammable region and above the AIT. The diluent will begin to burn spontaneously, causing a rapid and uncontrollable rise in reactor temperature, i.e., a runaway reaction. Obviously a reactor cannot be operated safely in this regime. Thus, in order to maximize epoxide production it is important to use find other diluents which allow for efficient removal of heat and safe operation under high oxygen conditions.

SUMMARY OF THE INVENTION

Figure 1:
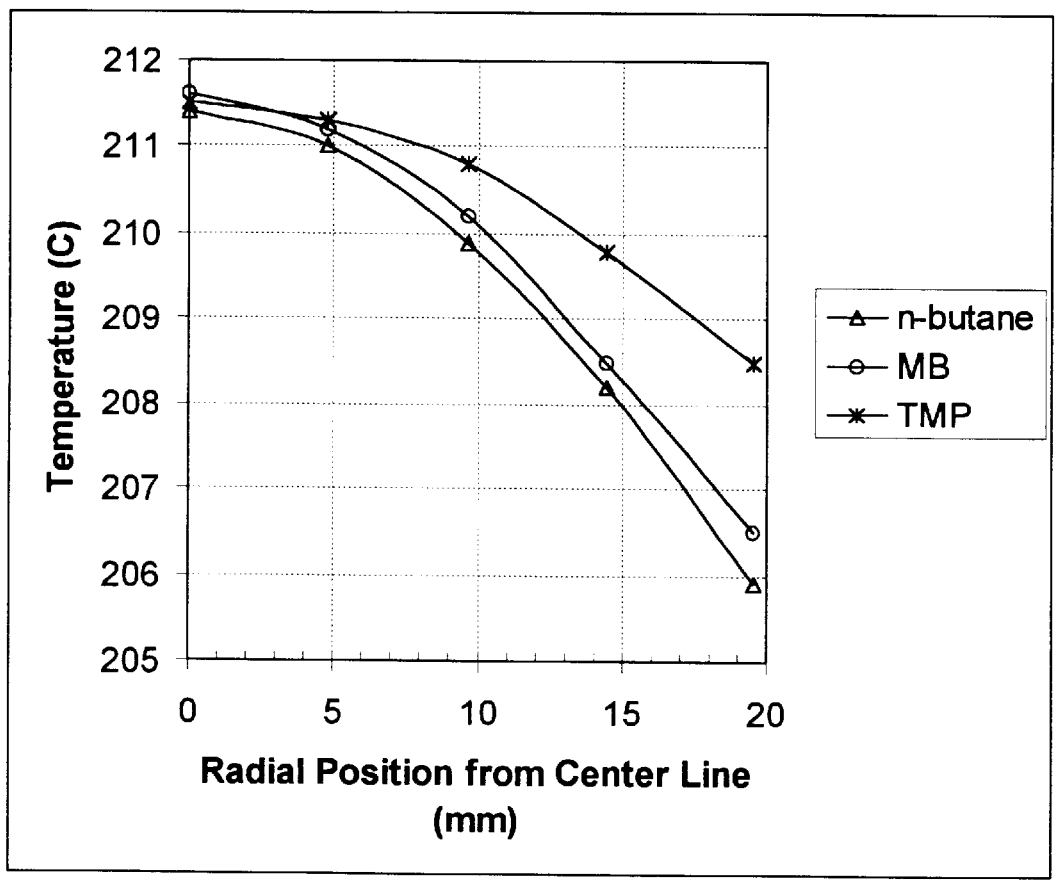
FIG. 1 is a plot of the radial temperature distribution at the point of the maximum axial temperature (hot spot temperature) for the diluents n-butane, 2-methyl-butane (MB), and 2,2,4-trimethyl-pentane (TMP). Each profile was estimated using a two-dimensional heat and mass transfer model for the epoxidation of butadiene to 3,4-epoxy-1-butene in a 6.1-meter, 19.5 mm inside diameter commercial reactor tube. For a given tube diameter, the temperature profile becomes flatter as the heat capacity of the diluent is increased in the series n-butane, 2-methyl-butane (MB), and 2,2,4-trimethyl-pentane (TMP).

This invention provides an improved gas phase process for the selective epoxidation of non-allylic olefins using heterogeneous catalysis wherein the epoxidation is carried out in the presence of branched-chain alkane or cyclic aliphatic hydrocarbons with high autoignition temperatures and high Research Octane Numbers. The hydrocarbons useful in the present invention possess higher heat capacities as compared to other non-oxidizable materials, e.g., nitrogen, argon, helium, and other straight-chain hydrocarbons, e.g., methane, ethane, and n-butane, as well as smaller flammability (cool flame and explosive) regions than the above-stated hydrocarbons typically used as diluents or ballast gases in olefin epoxidations.

DETAILED DESCRIPTION OF THE INVENTION

We have discovered that $C_5$ to $C_{10}$ branched-chain alkanes, cyclic aliphatic hydrocarbons with high autoiginition temperatures and high Research Octane Numbers (hereafter RON), and mixtures of branched-chain, straight-chain, and cyclic aliphatic hydrocarbons with high RON may be employed advantageously as inert diluents in the feed gas in the epoxidation of certain olefins. We have found that such diluents do not cause excessive chlorine stripping and subsequent loss of epoxidation selectivity. Rather the above-described hydrocarbon diluents surprisingly permit the use of high oxygen concentrations and higher reaction temperatures which promote increased epoxide production while decreasing the danger of approaching or entering the cool flame or explosive regions at normal reactor operating conditions. The use of such high-RON hydrocarbons as the inert diluent in accordance with the present invention permits oxygen concentrations of up to about 35 mole percent to be used safely, depending on the diluent selected, and the temperature and pressure at which the reaction is conducted. In contrast, the upper limit on oxygen concentration when using methane is about 18 mole percent and the upper limit with n-butane is less than 28 mole percent.

The autoignition temperature exhibited by a compound is highly dependent on the structure of that compound. Autoiginition temperature is lowered by increasing the number of carbon atoms in a homologous series, and is raised by increased branching in an isomeric grouping. Thus, the autoiginition temperature decreases in the homologous series n-butane>n-pentane>n-hexane as 372° C., 258° C., and 227° C. respectively, and increases with branching in the isomeric grouping 2,2-dimethyl-propane>2-methyl-pentane>n-pentane as 456° C., 420° C., and 258° C. respectively. Susceptibility to cool flame behavior is similar and hot flame or explosive limits are somewhat reduced when comparing straight-chain to branched chain isomers. For example, in air at 1 bar and 25° C. the upper explosive limits in the pentane isomer grouping are 2,2-dimethyl-propane<2-methyl-pentane <n-pentane as 7.5, 7.6, and 7.8 volume percent respectively. Another measure of the susceptibility to oxidation of a compound is the Research Octane Number (RON), defined as percentage of 2,2,4-trimethyl-pentane in a blend of n-heptane that gives the same engine knock intensity as the fuel under test when evaluated under standard conditions in a standard internal combustion engine. The RON is useful for measuring the susceptibility of mixtures of fuels to engine knocking in internal combustion engines and we have found it to be a measure of the susceptibility to oxidation of diluents in epoxidation reactions as well. (See, for example, *Automotive Fuels Reference Book,* by Keith Owen and Trevor Coley, 2nd ed., 1995, Society of Automotive Engineers, Inc. and *Petroleum Refinery Engineering,* by W. L. Nelson, pp. 31–32, and 179.)

The $C_5$ to $C_{10}$ branched-chain and cyclic hydrocarbons and high-RON mixtures employed in accordance with our invention also possess greater heat capacities than the commonly-used diluents referred to above. The higher heat capacity of the process gas permits the gas to absorb a larger amount of the heat generated by the exothermic epoxidation reaction, thereby enabling the epoxidation catalyst bed to be maintained at a lower temperature for a given production rate. This represents a significant advantage for commercial operations since a lower maximum reaction temperature allows operation of the reactor under safer conditions, extends the useful lifetime of the catalyst, and suppresses unwanted, thermal side reactions of the olefin reactant and oxygen. Furthermore, when using a high-RON diluent, a higher production rate of desired epoxide may be realized at the same reaction temperature or same temperature rise than may be attained with diluents having lower heat capacities. The use of process diluents having higher heat capacities also is advantageous relative to the design of the commercial reactor.

As is known to those skilled in the art, tubular reactors containing fixed beds of catalyst are the design of choice for vapor-phase, heterogeneous reaction systems. These reactors are operated in a wall-cooled configuration so that heat can be removed continuously, thereby approximating isothermality with the reactor. Isothermal or near-isothermal operation is preferred because the reaction conditions can be maintained within the sometimes narrow optimal temperature range. Operation of the reactor below optimal temperatures usually results in undesirably low reaction/production rates whereas operation above the optimal temperature range can cause poor selectivity and diminished operability due to thermal excursions or runaways. If the combination of diluent heat capacity and radial (through the wall) heat removal capability is insufficient to balance the heat of reaction, thermal runaways are likely to occur and a wall-cooled reactor design becomes impractical. Therefore, an important advantage in using a higher heat capacity diluent is the additional heat removal it provides to a wall-cooled reactor which in turn permits near-isothermal operation to be achieved and the optimal commercial reactor design to be employed. Since the heat of reaction is more efficiently transferred from the surface of the catalyst to the walls of the reactor, higher production rates may be realized for a given temperature when higher heat capacity hydrocarbon diluents according to the present invention are used in place of typically used diluent gases. The present invention enables production rates to be increased by up to 40% or higher, depending on the diluent selected, compared to the use of conventional diluents such as n-butane when total reaction temperature increases (total ΔT) are kept constant.

Thus, the present invention provides a continuous process for the preparation of the monoepoxide of an olefin reactant selected from norbornene, norbornadiene and olefins having the general formula

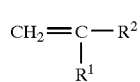

(I)

wherein $R^1$ is hydrogen or alkyl and $R^2$ is an aryl radical or the group

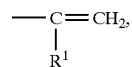

provided that the olefins of formula (I) contain more than 2 carbon atoms and do not contain any allylic hydrogen atoms, which comprises the steps of:

(1) continuously feeding a gas comprising about 3 to 30 mole percent of said olefin reactant, about 3 to 35 mole percent oxygen and about 35 to 90 mole percent of a branched-chain alkane or cyclic aliphatic hydrocarbon diluent containing 5 to 10 carbon atoms with an autoignition temperature at least 260° C. or above and Research Octane Numbers (RON) at least 75 or above, or a mixture of straight, branched, and cyclic aliphatics with RON at least 75 or above, wherein the oxygen:hydrocarbon diluent mole ratio is in the range of about 0.03:1 to 0.75:1 to an epoxidation zone containing a supported silver epoxidation catalyst and maintained at a temperature of about 1750 to 240° C.; and (2) continuously removing from the epoxidation zone a gas comprising about 0.5 to 4.5 mole percent of said monoepoxide of the olefin reactant, about 2 to 28 mole percent of said olefin reactant, about 2 to 33 mole percent oxygen and about 35 to 90 mole percent of said hydrocarbon diluent.

Since the olefin reactants employed in our novel process may be catalytically epoxidized at temperatures in the range of about 175 to 240° C., the problem of chloride stripping discussed above is not critical in the practice of our invention.

The supported silver epoxidation catalysts which may be used in the process provided by our invention are known materials which may be prepared according to published procedures including the catalyst manufacturing procedures described in U.S. Pat. Nos. 4,039,561, 4,169,009, 4,267,073, 4,389,338, 4,769,358, 5,081,096, and 5,362,890, incorporated herein by reference. Preferred catalysts useful in the present process comprise a catalyst support material having deposited on its surface about 1 to 30 weight percent silver and about 10 to 5000 parts per million by weight (ppmw) of an epoxidation catalyst modifier selected from alkali earth metals, alkaline earth metals and thallium. The support component of the catalysts may be selected from the large number of conventional, porous, refractory catalyst carriers or support materials which are essentially inert in the presence of the ethylenically unsaturated compound and oxygen-containing gas feeds and the products in the processes in which the catalysts are employed. Specific examples of suitable supports are the aluminum oxides (including the materials sold under the mark ALUNDUM by Norton Company, pumice, magnesia, zirconia, kieselguhr, fuller's earth, silicon carbide, porous agglomerates comprising silicon and/or silicon carbide, silica, selected clays, artificial and natural zeolites and ceramics. Refractory supports particularly useful in the preparation of the catalysts useful in the process of our invention comprise the aluminous materials, in particular those containing alpha alumina.

The olefin reactants which may be used in the process include norbornene, norbornadiene and olefins having the general formula

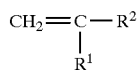
(I)

wherein R¹ is hydrogen or alkyl and R² is an aryl group, a tertiary alkyl group such as tertiary butyl, tertiary amyl, or tertiary octyl, or the group having the formula

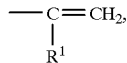

with the proviso that R¹ contains no hydrogen atoms in a position allylic to the ethylenic unsaturation, i.e., the >C═══C< group or groups. The alkyl groups represented by R¹ may be unsubstituted or substituted alkyl having up to about 12 carbon atoms. Such alkyl groups preferably are unsubstituted alkyl of up to about 4 carbon atoms. When the reactant is an olefin having the formula

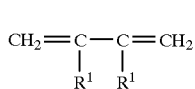
(I)

the R¹ substituents may be the same or different. The aryl groups represented by R² may be unsubstituted or substituted carbocyclic aryl having 6 to 10 carbon atoms, e.g., unsubstituted and substituted phenyl and naphthyl radicals. Examples of the substituents which may be present on the aryl groups include alkyl of up to about 4 carbon atoms, alkoxy of up to about 4 carbon atoms, halogen such as chloro and bromo, hydroxy, vinyl, and the like.

The epoxides produced from the olefins of formula (I) in accordance with the epoxidation process described herein have the general formula

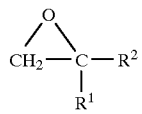
(II)

wherein R¹ and R² are defined above. The process provided by our invention is especially useful for the selective monoepoxidation of 1,3-butadiene to 3,4-epoxy-1-butene.

Our novel process may be carried out at a temperature in the range of about 175° to 240° C. with the range of 180° to 230° C. being particularly preferred. The pressure within the epoxidation zone may range from about 0.5 to 20 bars, preferably about 1 to 10 bar. The particular combination of temperature and pressure is selected so as to maintain all of the components of the feed to the epoxidation zone in the gaseous state.

The hydrocarbons which may be employed as inert diluents in the feed gas to the process of the present invention may be single-, double, triple, or quadruple-branched-chain alkanes or cyclic aliphatics containing 5 to 10 carbon atoms with autoignition temperatures of at least 260° C. and above and Research Octane Numbers at least 75 and above 75 or mixtures of straight, branched, and cyclic alkanes with RON at least 75 and above. The diluent employed in our invention may be a single component or a mixture of components. Preferably the autoignition temperature of the single component or mixture is at least 280° C. and the RON is at least 80. More preferably the autoignition temperature is temperature of the single component or mixture at least 300° C. and the RON is at least 85. Any mixtures of components may be used which meet the following criteria:

$\Sigma V_i R_i \geq 75$ preferably $\geq 80$, most preferably $\geq 85$.

Where $V_i$ is the volume percent of component i in the mixture and $R_i$ is the RON of component i and the product is summed from component 1 through the number of components in the mixture. Use of mixtures of components reduces the cost of the diluent stream and is advantageous. As noted above, while it is most preferred that the RON of the diluent is greater than or equal to 85, generally the upper useful limit for such diluents will be about 100. In a further embodiment, there are provided such hydrocarbon diluents which contain from 7 to 10 carbon atoms.

Specific examples of useful diluents include single-branched alkanes such as 2-methyl-butane (isopentane), double-branched alkanes such as 2,2-dimethylpropane (neopentane), 2,2-dimethyl-butane, 2,3-dimethyl-butane, 2,3-dimethyl-pentane, 2,3-dimethyl-hexane, 3,3-dimethyl-heptane, 2-methyl-3-ethyl-pentane, 2-methyl-4-ethyl-pentane, 3,3-diethyl-pentane, triple-branched alkanes such as 2,2,3-trimethyl-butane, 2,2,3-trimethyl-pentane, 2,2,4-trimethyl-pentane (isooctane), 2,3,3-trimethyl-pentane, 2,5,5-trimethyl-heptane, 2,4-dimethyl-3-ethyl-pentane, and quadruple-branched alkanes such as 2,2,3,3-tetramethylpentane, cyclic aliphatics such as cyclopentane, methyl-cyclopentane, and mixtures therein. 2-Methyl-butane, cyclopentane, methyl-cyclopentane, 2,2-dimethyl-butane and isomers, and 2,2,4-trimethylpentane and their isomers are preferred diluents because of their commercial availability and low cost.

As single-component diluents, the straight-chain hydrocarbons $C_5$–$C_{10}$, single-branched hexane, heptane, octane, nonane, decane isomers, 2-methyl-pentane, 3-methyl-pentane, 2-methyl-hexane, 3-methyl-hexane, 2-methyl-heptane, 2-methyl-octane, 3-methyl-octane, 4-methyl-octane, single-branched decane isomers, methyl-nonanes, ethyl-octanes, and double-branched 2,3-dimethyl-octane are not suitable as single-component diluents for our invention due to their low autoignition temperatures and low RON. Mixtures may consist of these components if the overall mixture RON meets the above mentioned criteria.

The advantages provided by the present invention, i.e., the use of relatively high concentrations of oxygen and increased heat transfer capabilities, may be achieved by feeding to the epoxidation zone a gas comprising about 3 to 30 mole percent of said olefin reactant, about 3 to 35 mole percent oxygen and about 35 to 90 mole percent of a branched-chain alkane or cyclic aliphatic hydrocarbon containing 5 to 10 carbon atoms with an autoignition temperature at least 260° C. or above and Research Octane Numbers (RON) at least 75 or above, or a mixture of straight, branched, and cyclic aliphatics with RON at least 75 or above, wherein the oxygen:alkane hydrocarbon mole ratio is in the range of about 0.03:1 to 0.75:1. Normally, the feed gas also will contain a total of about 0.5 to 10 mole percent of other components such as water, carbon dioxide, argon and recycled epoxide product. Up to about 10 mole percent of the inert diluent component of the feed gas may be made up of one or more other inert gases such as such as argon and nitrogen. In this context, an inert gas will be one which generally cannot be oxidized under the reaction conditions of the present invention. The feed gas to our novel continuous process preferably comprises (1) about 5 to 25 mole percent of the olefin reactant, (2) about 5 to 30 mole percent oxygen, (3) about 35 to 80 mole percent of the above-described hydrocarbon or mixture of hydrocarbons containing 4 to 10 carbon atoms and (4) a total of about 0.5 to 10 mole percent of other components selected from water, carbon dioxide, argon and recycled epoxide product. Thus, in a further aspect of the invention, there is provided a continuous process for the preparation of 3,4-epoxy-1-butene, which comprises the steps of:

(1) continuously feeding a gas comprising about 5 to 25 mole percent of 1,3-butadiene, about 5 to 30 mole percent oxygen and about 35 to 80 mole percent of a branched-chain alkane or cyclic aliphatic hydrocarbon diluent containing 5 to 10 carbon atoms with an autoignition temperature at least 260° C. or above and Research Octane Numbers (RON) at least 75 or above, or a mixture of straight, branched, and cyclic aliphatics with RON at least 75 or above, wherein the oxygen:hydrocarbon diluent mole ratio is in the range of about 0.03:1 to 0.75:1, and about 0.5 to about 10 mole percent of one or more components selected from water, carbon dioxide, argon, and recycled 3,4-epoxy-1-butene, to an epoxidation zone containing a supported silver epoxidation catalyst and maintained at a temperature of about 175° to 240° C.; and (2) continuously removing from the epoxidation zone a gas comprising about 0.5 to 4.5 mole percent of said 3,4-epoxy-1-butene, about 2 to 28 mole percent of 1,3-butadiene, about 2 to 33 mole percent oxygen and about 35 to 90 mole percent of said hydrocarbon diluent.

The selectivity of our novel epoxidation process may be increased by performing the process in the presence of halide, typically chloride, ion. Halide ion may be provided to the process by using a halide (chloride) salt of the modifier employed in the preparation of the catalysts. Alternatively, some or all of the halide ion may be provided to the process by including one or more organic halides in the gaseous feed, e.g., in a concentration of about 1 to 40 ppm. Examples of such useful organic halides are described in U.S. Pat. No. 5,362,890, incorporated herein by reference.

The novel process of the present invention is further illustrated by the following examples and computer simulations. The physical properties of the diluents used in the following examples are given in Table 1. The maximum safe oxygen percentage given therein is for a mixture of 1,3-butadiene, diluent, and nitrogen at the given butadiene:diluent:nitrogen ratio and at 210° C. and 2.62 bar.

COMPARATIVE EXAMPLE 1 AND EXAMPLES 1–3

N-butane, 2-methyl-butane (MB), and 2,2,4-trimethyl-pentane (TMP) diluents were compared as diluents for the epoxidation of 1,3-butadiene to 3,4-epoxy-1-butene. Conversions, selectivities, and reactor temperature profiles were determined for each diluent and at two levels of oxygen for 2-methylbutane.

The epoxidation catalyst employed comprised an alumina support in the form of 6 mm outside diameter rings having deposited thereon 12 weight percent silver and 700 parts per million by weight (ppmw) cesium. The catalyst was prepared according to known procedures by impregnating the support material with solutions of a silver amine salt and cesium chloride followed by a thermal decomposition/reduction treatment in the presence of an oxygen-containing gas to convert the silver salt to silver metal.

The epoxidation reaction was carried out in a reactor tube fabricated from Pyrex glass tubing of 30.5 cm length with an inside diameter of 10.2 mm. A portion of the above described silver/cesium/alumina catalyst rings was ground and sieved to provide catalyst granules having an irregular shape and a diameter ranging from about 1.0 to 3.2 mm. The charge (3 g) of these catalyst granules was held in place in the middle portion of the reactor tube by means of a constriction in the reactor diameter. The catalyst bed was 38 mm in length. A Chromel/Alumel alloy thermocouple sheathed in stainless steel was embedded within the middle of the catalyst bed to measure reaction temperature. The thermocouple was moveable, allowing temperature measurements anywhere within the catalyst bed. The reactor was heated by means of a tube furnace equipped with a temperature controller. The empty reactor volume above and below the catalyst bed was filled with Denstone ceramic particles to ensure that thermal reactions in such empty portions did not occur.

The reactor was operated at steady state conditions using a pressure of 1 bar absolute (1 atmosphere) in a single-pass, flow reactor. All normally gaseous components, i.e., n-butane, butadiene, oxygen, were fed to the reactor using mass flow controllers. Organic halide (2-chlorobutane) was added to the reactor feed gas in a stream of helium containing 100 parts per million by volume (ppmv) 2-chlorobutane. Thus, a mass flow controller was set to provide a flow rate that gave organic chloride concentrations of 3 ppmv in the feed gas.

MB and TMP, liquids at ambient temperatures, were fed to the epoxidation reactor by means of a helium-swept vapor-liquid equilibrium cell. The VLE cell consisted of a jacketed 500 ml stainless steel vessel fitted with a vapor inlet port and connected dip tube extending almost to the bottom of the cell, and a vapor outlet port. The VLE cell was to filled to approximately 80 percent of capacity with the desired diluent liquid, leaving some head space for equilibration and vapor-liquid disengagement. The position of the vapor inlet tube forced the sweep gas, i.e., helium, to pass through the body of the liquid and become saturated with the diluent liquid, before exiting the cell through the vapor outlet port. The feed rate of diluent was controlled by varying the helium sweep rate and the jacket temperature. Thus by careful control of the helium sweep rate (by mass flow controller) and VLE jacket temperature a known amount of diluent could be delivered to the reactor.

For each diluent tested, the total gas flow rate was maintained at approximately 100 standard cubic centimeters per minute and the maximum temperature in the reactor was maintained at 200° C. Although no helium was required for introduction of gaseous butane into the reactor, helium was added by a separate flow controller at a rate matching that required to introduce the MB into the reactor. The overall composition of the gas feed for each test condition is shown in Table 2.

Analyses of the reaction products and feed compositions were performed using an in-line gas sampling loop connected directly to the inlet of a gas chromatograph.

As used herein, conversion is the mole percent conversion of butadiene defined as:

$$\frac{\text{Moles butadiene converted to products}}{\text{Moles butadiene fed}} \times 100$$

and selectivity is the percent selectivity to 3,4-epoxy-1-butene defined as:

$$\frac{\text{Moles butadiene converted to 3, 4-epoxy-1-butene}}{\text{Moles butadiene converted to total products}} \times 100$$

Average conversions and selectivities for approximately 150 hours of operation under n-butane and MB, and 16 hours of operation under TMP are given in Table 3. Selectivities were approximately constant for each of the three diluents; no excessive chlorine stripping by the branched-chain diluents was observed, nor did the diluents burn under these reaction conditions. This held true for both low (16.5 percent) and high (30 percent) oxygen conditions for 2-methyl-butane.

COMPARATIVE EXAMPLE 2

The same reactor system and catalyst as described in Examples 1–3 and Comparative Example 1 were used to test the high temperature stability of reaction gas mixture containing n-hexane as diluents. N-hexane is a low-RON, low autoignition temperature diluent as shown in Table 1. A feed gas consisting of 16.5 mole percent oxygen, 8.1 mole percent 1,3-butadiene, 20 mole percent helium sweep gas and 55.1 mole percent vaporized n-hexane was fed to the reactor maintained at a maximum temperature of 200° C. Operation was stable with no uncontrollable exotherm. The furnace temperature was gradually increased and allowed to equilibrate. When the bed temperature reached 226° C., the temperature began to rise uncontrollably and within two minutes had reached 300° C., where upon the process was shut down. Although the oxygen concentration was well below the experimental upper explosive (hot flame) limit, the temperature was at or above the autoignition temperature and within the cool flame region, resulting in n-hexane combustion.

EXAMPLE 4

The same basic reactor system and catalyst as described in Examples 1–3 and Comparative Example 1 were used to test the high temperature stability of a reaction gas mixture containing 2-methyl-butane as diluent. 2-Methyl-butane is a high-RON, high-autoignition temperature diluent as shown in Table 1.

The reactor inside diameter was 6 mm and the catalyst bed height was 317.5 mm. The catalyst charge consisted of 12.87 g of 1.0 to 0.71 mm diameter particles. A feed gas consisting of 16.7 mole percent oxygen, 16.7 mole percent 1,3-butadiene, 12.1 mole percent helium sweep gas and the balance vaporized isopentane was fed to the reactor maintained at a maximum temperature of 200° C. and reached steady-state operation without incident. In spite of the high temperature and high conversion, selectivities remained comparable to low temperature operation. No evidence of runaway reaction or diluent burning was found. Results are given in Table 4.

COMPARATIVE EXAMPLE 3 AND EXAMPLES 5–6

Figure 2:
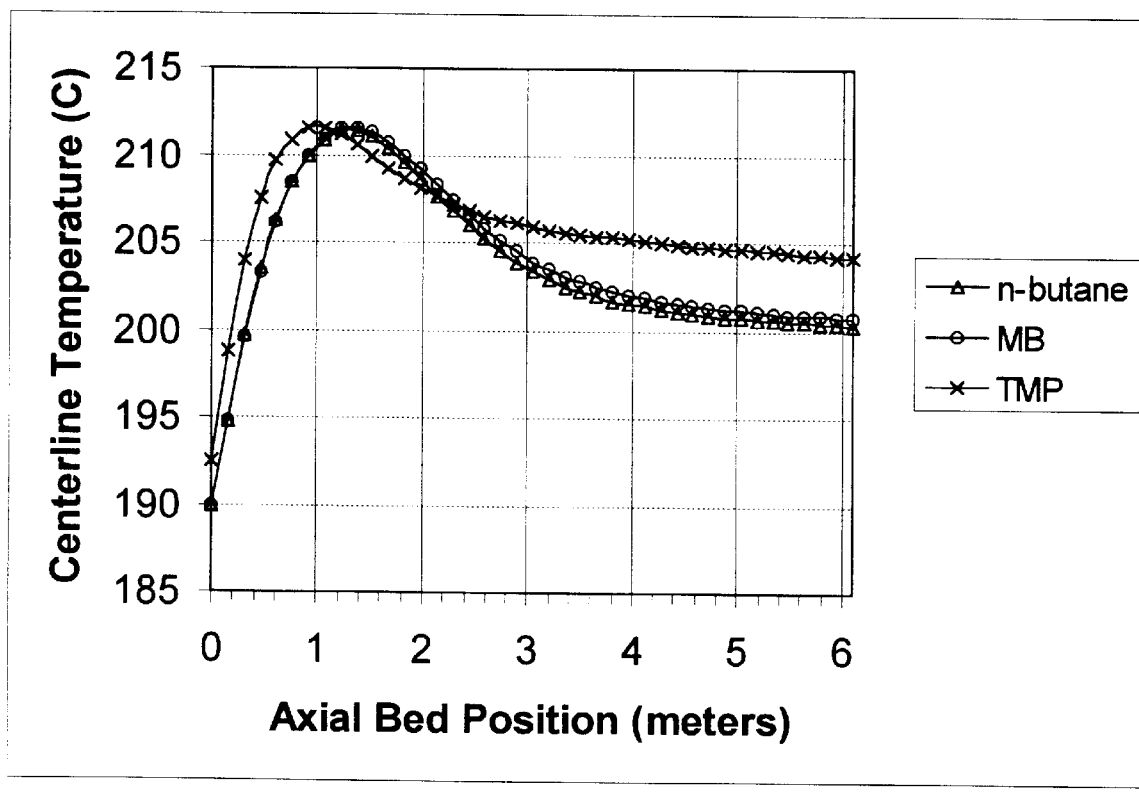
FIG. 2 is a plot of the centerline axial temperature distribution at constant hot spot temperature for the diluents n-butane, 2-methyl-butane (MB), and 2,2,4-trimethyl-pentane (TMP). Each profile was estimated using a two-dimensional heat and mass transfer model for the epoxidation of butadiene to 3,4-epoxy-1-butene in a 6.1-meter, 19.5 mm inside diameter commercial reactor tube. As the heat capacity of the diluent is increased in the series n-butane, 2-methyl-butane (MB), and 2,2,4-trimethyl-pentane (TMP), the average temperature of the bed is increased.

A computer simulation of a 6.1-meter commercial reactor tube, was conducted using kinetic parameters fitted for the epoxidation of 1,3-butadiene to 3,4-epoxy-1-butene using the same catalyst specified in Examples 1–3. A two-dimensional heat and mass transfer model of the epoxidation reaction found to be in excellent agreement with the experimentally measured conversions, selectivities, and temperature profiles. Computer simulation was used because of safety considerations with the large volume of gases involved in operating at the commercial scale. The computer simulation was used to determine the expected selectivity and conversion of 1,3-butadiene to 3,4-epoxy-1-butene at 85 percent of the maximum safe oxygen concentration (as given in Table 1) for n-butane, 2-methyl-butane, and 2,2,4-trimethyl-pentane at a maximum reactor temperature of 211.6° C. Feed conditions are given in Table 5. Cooling temperature refers to the temperature of the cooling media in the reactor jacket. All simulations were done with an inlet pressure of 3 bar. Simulation results are given in Table 6. Calculated axial and radial temperature profiles are shown in FIGS. 1 and 2. Because of their higher heat capacities and better flammability characteristics, 2-methyl-butane, and 2,2,4-trimethyl-pentane give increased conversions at similar selectivities and more uniform temperature profiles than n-butane for the same maximum reactor temperature.

COMPARATIVE EXAMPLES 4–5 AND EXAMPLES 7–8

These examples and counterexamples illustrate the difference conversion between n-butane and 2-methyl-butane for similar operating conditions. The same basic reactor system and catalyst as described in Examples 1–3 and Comparative Example 1 were used in Comparative Examples 4–5 and Examples 7–8.

The reactor inside diameter was 6 mm and the catalyst bed height was 317.5 mm. The catalyst charge consisted of 12.87 g of 1.0 to 0.71 mm diameter particles. A feed gas consisting of 16.7 mole percent oxygen, 16.7 mole percent 1,3-butadiene, 12.1 mole percent helium sweep gas and the balance vaporized 2-methyl-butane or gaseous n-butane was fed into the reactor. The oven temperature was adjusted to maintain a maximum temperature of about 190° C. for all of the above examples. Results are given in Table 7 for two flow rates for each of the 2-methyl-butane and n-butane.

TABLE 1

| Diluent | Autoignition Temperature (°C.) | Research Octane Number (RON) | Molar Heat Capacity at 200° C. (cal-gmole-°C.) | Maximum Safe Oxygen Percentage | Butadiene: Diluent: Nitrogen Ratio |
|---|---|---|---|---|---|
| n-butane | 372 | 93.6 | 33.4 | 28 | 9:48:15 |
| 2-methyl-butane | 420 | 92.3 | 41.5 | 31 | 9:45:15 |
| 2,2,4-trimethyl-pentane | 418 | 100 | 49.1 | 35 | 9:41:15 |
| n-hexane | 227 | 24.8 | 67.3 | 24 | 9:52:15 |

TABLE 2

| Example | Diluent | Mole Percent Diluent in Feed | Mole Percent Oxygen in Feed | Mole Percent Butadiene in Feed | Mole Percent Helium in Feed |
|---|---|---|---|---|---|
| Comparative Example 1 | N-butane | 55.1 | 16.5 | 8.1 | 20.0 |
| Example 1 | 2-Methyl-butane | 55.1 | 16.5 | 8.1 | 20.0 |
| Example 2 | 2-Methyl-butane | 43.7 | 30.0 | 8.6 | 16.7 |
| Example 3 | 2,2,4-Trimethyl-pentane | 51.3 | 17.3 | 8.5 | 22.5 |

TABLE 3

| Example | Diluent | Percent Butadiene Conversion | Selectivity |
|---|---|---|---|
| Comparative Example 1 | N-butane | 20.3 | 90.8 |
| Example 1 | 2-Methyl-butane | 20.6 | 90.2 |
| Example 2 | 2-Methyl-butane | 26.2 | 90.0 |
| Example 3 | 2,2,4-Trimethyl-pentane | 23.7 | 90.2 |

TABLE 4

| Example | Diluent | Maximum Bed Temperature (°C.) | Selectivity | Conversion |
|---|---|---|---|---|
| Example 4a | 2-methylbutane | 225.7 | 86.9 | 27.1 |
| Example 4b | 2-methylbutane | 227.6 | 86.6 | 27.1 |

TABLE 5

| Example | Diluent | Inlet Gas Temperature (°C.) | Cooling Temperature (°C.) | Percentage Oxygen Fed | Percentage Diluent |
|---|---|---|---|---|---|
| Comparative Example 3 | n-butane | 190.0 | 197.0 | 24.0 | 52 |
| Example 5 | 2-methyl-butane | 190.0 | 197.5 | 26.5 | 49.5 |
| Example 6 | 2,2,4-trimethyl-pentane | 192.0 | 202.0 | 30.0 | 46.0 |

TABLE 6

| Example | Diluent | Maximum Temperature (°C.) | Selectivity | Conversion | Percent Increase in Conversion over n-butane |
|---|---|---|---|---|---|
| Comparative Example 3 | n-butane | 211.6 | 90.8 | 31.2 | — |
| Example 5 | 2-methyl-butane | 211.6 | 90.7 | 35.0 | 12 |
| Example 6 | 2,2,4-trimethyl-pentane | 211.5 | 90.0 | 43.6 | 40 |

TABLE 7

| Example | Diluent | Flow Rate (SCCM) | Maximum Temperature (°C.) | Selectivity | Conversion | Percent Increase in Conversion over n-butane |
|---|---|---|---|---|---|---|
| Comparative Example 4 | n-butane | 202 | 189.8 | 89.7 | 22.2 | — |
| Example 5 | n-butane | 104 | 190.4 | 87.9 | 21.6 | 5.4 |
| Example 7 | 2-methyl-butane | 200 | 190.4 | 89.7 | 23.4 | — |
| Example 8 | 2-methyl-butane | 104 | 191.0 | 87.3 | 24.4 | 12.7 |

The invention has been described in detail with particular reference to preferred embodiments thereof, but it will be understood that variations and modifications may be effected within the spirit and scope of the invention.

We claim:

1. A continuous process for the preparation of the monoepoxide of an olefin reactant selected from norbornene, norbornadiene and olefins having the general formula $$CH_2 = C - R^2 \atop | \atop R^1 \qquad (I)$$

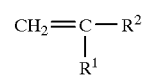

wherein $R^1$ is hydrogen or alkyl and $R^2$ is an aryl radical or the group

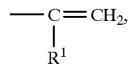

$$-C = CH_2, \atop | \atop R^1$$

provided that the olefins of formula (I) contain more than 2 carbon atoms and do not contain any allylic hydrogen atoms, which comprises the steps of:

(1) continuously feeding a gas comprising about 3 to 30 mole percent of said olefin reactant, about 3 to 35 mole percent oxygen and about 35 to 90 mole percent of a branched-chain alkane or cyclic aliphatic hydrocarbon diluent containing 5 to 10 carbon atoms with an autoignition temperature at least 260° C. or above and Research Octane Numbers (RON) at least 75 or above, or a mixture of straight, branched, and cyclic aliphatics with RON at least 75 or above, wherein the oxygen: hydrocarbon diluent mole ratio is in the range of about 0.03:1 to 0.75:1 to an epoxidation zone containing a supported silver epoxidation catalyst and maintained at a temperature of about 175° to 240° C.; and (2) continuously removing from the epoxidation zone a gas comprising about 0.5 to 4.5 mole percent of said monoepoxide of the olefin reactant, about 2 to 28 mole percent of said olefin reactant, about 2 to 33 mole percent oxygen and about 35 to 90 mole percent of said hydrocarbon diluent.

2. The process of claim 1, wherein said hydrocarbon diluent contains from 7 to 10 carbon atoms.

3. The process of claim 1, wherein the temperature of said process is from about 180° to 230° C.

4. The process of claim 1, wherein the pressure within said epoxidation zone is about 1 to 10 bar.

5. The process of claim 1, wherein the autoignition temperature of said hydrocarbon diluent is at least 280° C. and the RON is at least 80.

6. The process of claim 1, wherein the autoignition temperature of said hydrocarbon diluent is at least 300° C. and the RON is at least 85.

7. The process of claim 1, wherein said hydrocarbon diluent is one or more compounds selected from the group consisting of 2-methyl-butane, 2,2-dimethylpropane, 2,2-dimethyl-butane, 2,3-dimethyl-butane, 2,3-dimethyl-pentane, 2,3-dimethyl-hexane, 3,3-dimethyl-heptane, 2-methyl-3-ethyl-pentane, 2-methyl-4-ethyl-pentane, 3,3-diethyl-pentane, 2,2,3-trimethyl-butane, 2,2, 3-trimethyl-pentane, 2,2,4-trimethyl-pentane, 2,3,3-trimethyl-pentane, 2,5,5-trimethyl-heptane, 2,4-dimethyl-3-ethyl-pentane, 2,2, 3,3-tetramethyl-pentane, cyclopentane, and methyl-cyclopentane.

8. The process of claim 1, wherein said hydrocarbon diluent is one or more compounds selected from the group consisting of 2-methyl-butane, 2,2-dimethyl-butane, and 2,3-dimethyl-butane.

9. The process of claim 1, wherein said hydrocarbon diluent is selected from the group consisting of 2,3-dimethyl-pentane, 2,3-dimethyl-hexane, 3,3-dimethyl-heptane, 2-methyl-3-ethyl-pentane, 2-methyl-4-ethyl-pentane, 3,3-diethyl-pentane, 2,2,4-trimethyl-butane, 2,2,3-trimethyl-pentane, 2,2,4-trimethyl-pentane, 2,3,3-trimethyl-pentane, 2,5,5-trimethyl-heptane, 2,4-dimethyl-3-ethyl-pentane, 2,2,3,3-tetramethyl-pentane, cyclopentane, and methyl-cyclopentane.

10. The process of claim 1, wherein said hydrocarbon diluent is 2,2,4-trimethylpentane.

11. The process of claim 1, wherein the olefin reactant of formula (I) is 1,3-butadiene.

12. A continuous process for the preparation of 3,4-epoxy-1-butene, which comprises the steps of:

(1) continuously feeding a gas comprising about 5 to 25 mole percent of 1,3-butadiene, about 5 to 30 mole percent oxygen and about 35 to 80 mole percent of a branched-chain alkane or cyclic aliphatic hydrocarbon diluent containing 5 to 10 carbon atoms with an autoignition temperature at least 260° C. or above and Research Octane Numbers (RON) at least 75 or above, or a mixture of straight, branched, and cyclic aliphatics with RON at least 75 or above, wherein the oxygen:hydrocarbon diluent mole ratio is in the range of about 0.03:1 to 0.75:1, and about 0.5 to about 10 mole percent of one or more components selected from water, carbon dioxide, argon, and recycled 3,4-epoxy-1-butene, to an epoxidation zone containing a supported silver epoxidation catalyst and maintained at a temperature of about 175° to 240° C.; and (2) continuously removing from the epoxidation zone a gas comprising about 0.5 to 4.5 mole percent of said 3,4-epoxy-1-butene, about 2 to 28 mole percent of 1,3-butadiene, about 2 to 33 mole percent oxygen and about 35 to 90 mole percent of said hydrocarbon diluent.

13. The process of claim 12, wherein said hydrocarbon diluent contains from 7 to 10 carbon atoms.

14. The process of claim 12, wherein the temperature of said process is from about 180° to 230° C.

15. The process of claim 12, wherein the pressure within said epoxidation zone is about 1 to 10 bar.

16. The process of claim 12, wherein the autoignition temperature of said hydrocarbon diluent is at least 280° C. and the RON is at least 80.

17. The process of claim 12, wherein the autoignition temperature of said hydrocarbon diluent is at least 300° C. and the RON is at least 85.

18. The process of claim 12, wherein said hydrocarbon diluent is one or more compounds selected from the group consisting of 2-methyl-butane, 2,2-dimethylpropane, 2,2-dimethyl-butane, 2,3-dimethyl-butane, 2,3-dimethyl-pentane, 2,3-dimethyl-hexane, 3,3-dimethyl-heptane, 2-methyl-3-ethyl-pentane, 2-methyl-4-ethyl-pentane, 3,3-diethyl-pentane, 2,2,3-trimethyl-butane, 2,2,3-trimethyl-pentane, 2,2,4-trimethyl-pentane, 2,3,3-trimethyl-pentane, 2,5,5-trimethyl-heptane, 2,4-dimethyl-3-ethyl-pentane, 2,2,3,3-tetramethyl-pentane, cyclopentane, and methyl-cyclopentane.

19. The process of claim 12, wherein said hydrocarbon diluent is one or more compounds selected from the group consisting of 2-methyl-butane, 2,2-dimethyl-butane, and 2,3-dimethyl-butane.

20. The process of claim 12, wherein said hydrocarbon diluent is selected from the group consisting of 2,3-dimethyl-pentane, 2,3-dimethyl-hexane, 3,3-dimethyl-heptane, 2-methyl-3-ethyl-pentane, 2-methyl-4-ethyl-pentane, 3,3-diethyl-pentane, 2,2,3-trimethyl-butane, 2,2,3-trimethyl-pentane, 2,2,4-trimethyl-pentane, 2,3,3-trimethyl-pentane, 2,5,5-trimethyl-heptane, 2,4-dimethyl-3-ethyl-pentane, 2,2,3,3-tetramethyl-pentane, 2,2,3,3-tetramethyl-pentane, cyclopentane, and methyl-cyclopentane.

21. The process of claim 12, wherein said hydrocarbon diluent is 2,2,4-trimethylpentane.

* * * * *